(12) United States Patent
Herry et al.

(10) Patent No.: US 10,987,309 B2
(45) Date of Patent: Apr. 27, 2021

(54) TABLET CAPABLE OF COMBATTING MISUSE BY INJECTION

(71) Applicant: ETHYPHARM, Saint-Cloud (FR)

(72) Inventors: Catherine Herry, Saint-Ouen du Tilleul (FR); Pauline Contamin, La Feuillie (FR)

(73) Assignee: ETHYPHARM, Saint-Cloud (FR)

( * ) Notice: Subject to any disclaimer, the term of this patent is extended or adjusted under 35 U.S.C. 154(b) by 0 days.

(21) Appl. No.: 14/363,700

(22) PCT Filed: Dec. 6, 2012

(86) PCT No.: PCT/EP2012/074671
§ 371 (c)(1),
(2) Date: Jun. 6, 2014

(87) PCT Pub. No.: WO2013/083710
PCT Pub. Date: Jun. 13, 2013

(65) Prior Publication Data
US 2014/0322321 A1    Oct. 30, 2014

(30) Foreign Application Priority Data
Dec. 6, 2011 (FR) ...................................... 1161249

(51) Int. Cl.
*A61K 9/20* (2006.01)
*A61K 31/485* (2006.01)
*A61K 9/28* (2006.01)

(52) U.S. Cl.
CPC ............ *A61K 9/2027* (2013.01); *A61K 9/205* (2013.01); *A61K 9/2031* (2013.01); *A61K 9/2866* (2013.01); *A61K 9/2893* (2013.01); *A61K 31/485* (2013.01); *A61K 9/2086* (2013.01)

(58) Field of Classification Search
CPC ............................ A61K 31/485; A61K 8/2054
See application file for complete search history.

(56) References Cited

U.S. PATENT DOCUMENTS

| 4,070,494 | A | 1/1978 | Hoffmeister et al. | |
| 7,276,250 | B2* | 10/2007 | Baichwal et al. | 424/468 |
| 2005/0031546 | A1 | 2/2005 | Bartholomaus et al. | |
| 2009/0099154 | A1* | 4/2009 | Jain et al. | 514/217 |
| 2010/0015223 | A1* | 1/2010 | Cailly-Dufestel et al. | 424/472 |
| 2010/0291202 | A1* | 11/2010 | Ravishankar et al. | 424/456 |
| 2012/0202838 | A1* | 8/2012 | Ghosh et al. | 514/282 |
| 2012/0321674 | A1* | 12/2012 | Vachon | A61K 31/485 424/400 |
| 2012/0321716 | A1* | 12/2012 | Vachon | A61K 9/2054 424/490 |
| 2013/0022646 | A1* | 1/2013 | Rudnic | A61K 45/06 424/400 |

FOREIGN PATENT DOCUMENTS

| WO | WO 03/013476 A1 | 2/2003 |
| WO | WO 2007/000779 A2 | 1/2007 |
| WO | WO 2007/099152 A1 | 9/2007 |

OTHER PUBLICATIONS

Lubrizol, "Lubrizol pharmaceutical polymers for controlled release tablets and capsules", Pharmaceutical Bulletin 30, May 31, 2011. (Year: 2011).*
International Search Report in Application No. PCT/EP2012/074671, dated Apr. 3, 2013.

* cited by examiner

*Primary Examiner* — Gina C Justice
(74) *Attorney, Agent, or Firm* — Dinsmore & Shohl LLP

(57) ABSTRACT

The invention relates to an oral pharmaceutical composition in the form of a sustained-release tablet comprising an active ingredient capable of being misused, which composition makes it possible to combat misuse by injection.

15 Claims, No Drawings

TABLET CAPABLE OF COMBATTING MISUSE BY INJECTION

CROSS REFERENCE TO RELATED APPLICATIONS

This application is a 371 application of International Application No. PCT/EP2012/074671, filed Dec. 6, 2012, which claims priority to French Application 1161249, filed Dec. 6, 2011, all of which are incorporated by reference in its entirety herein.

Drug abuse is the intentional misuse by drug addicts of certain drugs, in particular come psychotropic or narcotic agents such as opioids or the derivatives thereof used in therapy to treat severe pain or to treat addiction to opiate drugs.

For misuse via injection, the tablet or capsule containing the active ingredients of interest is reduced to a fine power using any possible means at hand for a drug addict, in particular a mortar or cigarette lighter, even by chewing or biting into the tablet. The coarse powder obtained, which necessarily contains the initial excipients included in the pharmaceutical form, can then be dissolved in a small volume of liquid (a few millilitres) at times previously heated, and/or with the addition of an acid for some active ingredients present in their base form (brown heroin, morphine base). The liquid obtained can then be roughly filtered to limit entry into the blood of large particles using a cigarette filter for example before being injected via intravenous route.

In this case, the active ingredient is immediately available in the blood, providing the immediate psychotropic effect sought after by a drug addict.

Drug abuse is also accompanied by numerous health risks directly related to the injection of excipients and crushing residues that are not purified, ill- or hardly filtered and non-sterile.

Application WO2007099152 is known in the state of the art. This application concerns sustained-release matrix tablets that are water-insoluble and ultra-hard. These matrix tablets comprise an active ingredient dispersed in a compression matrix formed of at least one excipient selected from the group comprising water-insoluble, pH-independent sustained-release polymers, mineral excipients and the mixtures thereof.

Such tablets can prevent phenomena of involuntary misuse when the tablet is taken with alcohol or when accidentally chewed by a patient. The tablets described in WO2007099152 also prevent drug abuse by preventing deliberate misuse of the active ingredient via oral and nasal route.

However, these tablets do not allow misuse of active ingredient via injectable route.

Document U.S. Pat. No. 4,070,494 is also known in the state of the art. This document relates to pharmaceutical compositions which prevent misuse of active ingredients via parenteral route by limiting active ingredient extraction in the presence of water. These compositions comprise an excipient which gels in water.

However, in this document no solution is given to prevent active ingredient extraction in an acid or hydro-alcoholic medium.

Oxycontin® is also known, a tablet of oxycodone that is widely misused by drug addicts. Its formulation was reviewed to limit abuse. However, even after reformulation, misuse by injection is still possible.

There is therefore a true need for the development of a pharmaceutical composition which makes active ingredient extraction difficult end even impossible from all liquid media, whether aqueous (irrespective of pH) or hydro-alcoholic, in particular hydrochloric acid, vinegar, lemon juice, 40% ethanol, 50% ethanol, 60% ethanol, 70% ethanol, 60% ethanol, 90% ethanol and 96% ethanol.

This pharmaceutical form must also be produced using an extremely simple manufacturing process that is rapid and low cost.

The objective of the present invention is therefore to propose a sustained-release solid, oral pharmaceutical composition for use as medicinal product to combat misuse via injectable route.

The subject of the invention is therefore an oral pharmaceutical product in sustained-release tablet form comprising:
at least one active ingredient likely to be misused for drug addiction;
a mixture of polyvinyl acetate and polyvinylpyrrolidone, xanthan gum,
a carbomer and/or gum arabic.

Definitions

In the present invention, by «sustained-release» is meant the release of one or more active ingredients into the body over periods longer than 6 hours, preferably longer than 8 hours, even a period longer than 24 hours making the administration of these active ingredients possible either in two daily doses or a single daily dose.

In the present invention, the terms intentional misuse of drug-abuse are used to designate any deliberate alteration of the preparatory forms. In particular, the notion of intentional misuse concerns the reducing of tablets to powder followed by their dissolving in a small amount of liquid for the purpose of parenteral injection.

Preferably, by «combatting misuse by injection» is meant that the amount of active ingredient extracted in a hydro-alcoholic medium is lower than the amount contained in Oxycontin®, i.e. less than 40% of active ingredient is extracted. The amount of active ingredient extracted in an aqueous medium is lower than that contained in Oxycontin®, i.e. less than 25% of active ingredient is extracted.

By «aqueous solution» is meant any liquid medium irrespective of its pH: acid, neutral or basic, containing at least one part water. As examples, mention can be made of water, vinegar, lemon juice, soft drinks, etc.

In the present invention the expression «hydro-alcoholic solution» is defined as any liquid medium containing at least part water and part ethanol such as 40% ethanol, 50% ethanol, 60% ethanol, 70% ethanol, 80% ethanol, 90% ethanol and 96% ethanol.

By «carbomer» or «Carbopol®» is meant a polymer of acrylic acid of high molecular weight cross-linked with allyl sucrose or allyl ethers of pentaerythritol (Handbook of Pharmaceutical Excipients, $5^{th}$ Edition, p. 111). For example, it may be carbomer 910, carbomer 934, carbomer 934P, carbomer 940, carbomer 941, carbomer 71G, carbomer 980, carbomer 971P or carbomer 974P. The viscosity of the said carbomer is between 4000 and 60000 cP at 0.5% w/w.

In the present invention by «tablet» is meant matrix tablets, multilayer tablets, micro-tablets.

Description

The composition according to the invention may contain one or more active ingredients likely to be misused and which may be of any type. Advantageously the chosen active ingredients are intended to be released into the body over a long period i.e. over periods of at least 6 hours, and preferably more than 12 hours, further preferably more than 20 hours.

Therefore the tablets according to the invention are preferably used for the sustained delivery of active ingredients belonging to the family of psychotropic agents i.e that are psychoactive via stimulating, tranquillizing or hallucinogenic effects.

For example the active ingredients which can be used in the invention are preferably derivatives and/or alkaloids of opium, whether natural or synthetic, such as codeine, narceine, noscapine and the salts thereof.

The active ingredients which can be used in the invention also belong to the group comprising morphine, its derivatives and the salts thereof and in particular morphinenes such as pholcodine, nalorphine, codeine, hydrocodone, pholcodine, dihydrocodeine, hydromorphone, and morphinans such as buprenorphine, butorphanol, dextromethorphan, nalbuphine, naltrexone, naloxone, nalmefene, hydrocodone, oxymorphone and oxycodone, and in general all analogues of morphine such as fentanyl, alfentanyl, sufentanyl, tramadol, apomorphine and etorphine.

The present invention also addresses alkaloid derivatives, natural or synthetic, having a psychotropic effect such as cocaine and its derivatives, heroin, cannabis and cannabinoids.

Finally, the present invention also addresses all the substances currently used in therapeutics as substitution treatment for drug addiction and assisted withdrawal, such as methadone and buprenorphine for example that are very widely misused.

In general, the present invention can also be envisaged for all other therapeutic drug classes that are subject to misuse at the present time, and in particular antipsychotics, tranquillizers, hypnotics, analgesics, anxiolytics, in particular the class of benzodiazepines, amphetaminics.

The active ingredient(s) contained in the composition represent between 1 and 70% by weight of the total weight of the composition. Advantageously the active ingredient(s) represent 5 to 50% by weight of the total weight of the composition and further advantageously 10% to 40% by weight of the total weight of the composition.

It is also possible to quantify the active ingredient in milligrams (mg). Therefore the active ingredient(s) contained in the composition represent between 0.1 mg and 500 mg in the tablet. Advantageously the active ingredient(s) represent 1 mg to 200 mg in the tablet. For example a tablet of oxycodone contains 5 to 80 mg of oxycodone.

For example a tablet of hydromorphone contains 4 to 64 mg of hydromorphone and a morphine tablet contains 5 to 200 mg of morphine.

The active ingredient(s) contained in the composition of the invention may be present in any form known to persons skilled in the art, and in particular in powder, crystal or granule form.

The composition according to the invention also contains a mixture of polyvinyl acetate and polyvinylpyrrolidone. The ratio of polyvinyl acetate and polyvinylpyrrolidone in the mixture is between (95:5) and (70:30), preferably it is (80:20).

The mixture of polyvinyl acetate (PVA) and polyvinylpyrrolidone (PVP) represents 10 to 80% by weight of the total weight of the composition, preferably 15 to 70% by weight of the total weight of the composition and further preferably 20 to 60% by weight of the total weight of the composition.

Xanthan gum is also present in the composition of the invention. It represents 1 to 88% by weight of the total weight of the composition, particularly 3 to 50% by weight of the total weight of the composition, preferably 10 to 40%, more preferably 5 to 30%, and further preferably 15 to 25%.

The composition according to the invention further comprises a carbomer (Carbopol®) and/or gum arabic. The quantities of carbomer and/or gum arabic represent 1 to 88% by weight of the total weight of the composition, in particular 2 to 50%, preferably 5 to 40%, more preferably 8 to 30%, further preferably 10 to 30% by weight of the total weight of the composition.

Surprisingly the inventors have found that the specific association of the above-described compounds allows prevented misuse by injection when the pharmaceutical form is reduced to powder for the purpose of being dissolved in an injectable volume of an aqueous or hydro-alcoholic solution.

When the composition of the present intention is reduced to powder form and then placed in an aqueous solution (even at pH<3) or hydro-alcoholic solution, a gel is formed trapping the active ingredient and making administration via parenteral route difficult.

In addition, on seeing the thickness of the gel formed a drug addict will be strongly deterred from self-injecting such a composition.

Also, since this composition is insoluble in an alcohol medium, this avoids the massive release of active ingredient into the body in the event of concomitant ingestion of alcohol and provides against accidental misuse.

Another advantage of this composition is that it limits misuse via nasal route. When the composition is reduced to powder for absorption via nasal route, a gel is formed in contact with mucous secretions thereby trapping the active ingredient.

The pharmaceutical composition of the present invention also has a crush resistance of at least 4 MPa, advantageously at least 6 MPa. In the present application the notion will be used both of a crush resistance and of hardness such as described in application WO2007099152 to characterize the tablets.

Through its crush resistance, the composition of the invention allows the limiting of misuse via oral route. The composition has a structure which limits risk of being crushed with conventionally used techniques by drug addicts (crushing under a cup or between two spoons) or by chewing.

According to another aspect the inventors were also surprised to ascertain that if a pH-modifying agent is added to the composition of the present invention, and when the composition is reduced to powder and placed in an aqueous or hydro-alcoholic solution, the resulting gel has a viscosity such that the gel can no longer pass through a 20 gauge needle. This property is remarkable since it eradicates any attempt for administration by injection.

The pH-modifying agent of the invention comprises at least one of the following compounds: citric acid, sodium bicarbonate, fumaric acid, sodium phosphate, potassium hydroxide, sodium hydroxide and sodium carbonate.

For example the present pharmaceutical composition may comprise 0.1 to 30% by weight of pH-modifying agent in the total weight of the composition, preferably 0.5 to 20% by weight of pH-modifying agent in the total weight of the composition and more preferably 1 to 10% by weight of pH-modifying agent in the total weight of the composition.

Advantageously, it was also ascertained that the presence of pH-modifying agent can make release of the active ingredient pH-independent when it travels through the gastro-intestinal tract. Therefore the release of active ingredient cannot be perturbed by variations in pH of the different media.

The said pharmaceutical composition may also comprise at least one of the following substances (a) to (e) or a mixture thereof:
  (a) a substance which irritates the nasal and/or pharyngeal pathways;
  (b) an antagonist of the active ingredient(s) likely to be misused for drug addiction means;
  (c) an emetic substance;
  (d) a colouring agent as aversive agent;
  (e) a substance of bitter taste.

When the active ingredient is a natural or synthetic opiate derivative, the antagonist is advantageously chosen from the group comprising naloxone, naltrexone, nalmefene, nalid, nalmexone, nalorphine and naluphine, these different compounds each being in pharmaceutically acceptable form, in particular in the form of base, salt or in solvate form. These antagonists are present in doses conventionally used in particular in a proportion of 0.5 to 100 mg per composition.

In one advantageous embodiment of the invention the said antagonist agent is naloxone or one of its pharmaceutically acceptable salts.

According to one particular embodiment of the invention, the composition can be film-coated with an outer coating which those skilled in the art will know how to adapt in relation to the needs and allocated function of this coating.

For example the outer coating can be applied for the purpose of protecting the active ingredient if the active ingredient is sensitive to the low pH values of the gastric medium for example, in which case the term gastro-resistant coating is used.

In addition, the outer coating can be applied to further slow the diffusion of the active ingredient. For this purpose different grades of ethylcellulose or methacrylic polymers can be used, well known to persons skilled in the art.

Finally, the outer coating can be used to modify the appearance (texture, colour) and/or palatability (sensation in the mouth) of the composition for a patient. In particular, advantageous use can be made of excipients such as cellulose derivatives or acrylic derivatives well known to skilled persons to mask the taste of the active ingredient if necessary.

Said coating may therefore comprise a mixture of one or more excipients of different type known to persons skilled in the art, used alone or in a mixture for the different functions listed above.

The excipient(s) used for the coating are applied in a manner known to skilled person in the necessary amount to obtain the desired function(s).

These excipients can be applied to the surface of the composition as is conventional by spraying a solution or suspension of the coating agent in a solvent, in a perforated drum or fluidised bed for example.

The composition according to the invention can adapt to all preparatory forms, in particular it can be in the form of a matrix tablet, multilayer tablet or micro-tablet.

Matrix Tablet

The term «matrix» is used to designate a pharmaceutical composition whose inner structure is homogeneous and identical from the centre towards the periphery of the composition.

The composition of the present invention is composed of a homogeneous mixture or active ingredient in powder or granule form and of at least a mixture of polyvinyl acetate and polyvinylpyrrolidone associated with xanthan gum and Carbopol and/or gum arabic.

More particularly the active ingredient(s) can be directly added to the mixture to be compressed, mounted on carriers (to obtain microgranules) or granulated via wet or dry process (to obtain granules).

If the active ingredient(s) are present in the form of microgranules, these microgranules can be conventionally obtained by deposit (mounting) of the active ingredient(s) on the surface or pharmaceutically neutral carriers such as prefabricated cellulose-based micro-beads or a mixture of sugar and starch sold under the name "sugar spheres", or granules of other excipients such as lactose for example.

The depositing (mounting) process of the active ingredient is performed in conventional manner known to persons skilled in the art and can vary in relation to the type, the quantity and the fragility of the active ingredient(s) to be deposited. For example depositing can be performed by spraying a solution or suspension of the active ingredient(s) onto the surface of the neutral carrier, or spraying of the active ingredient(s) in powder onto the surface of the carrier previously moistened with a binding agent solution.

The granules of active ingredient(s) can also be obtained by dry or wet granulation of the active ingredient(s) of interest, generally in the presence of at least one binding agent and optionally a wetting liquid depending on techniques, these also being well known to those skilled in the art. This granulation step improves the uniformity of the content of the tablets produced.

The granules obtained are mixed with:
  the mixture of polyvinyl acetate and polyvinylpyrrolidone;
  xanthan gum; and
  Carbopol and/or gum arabic,
and the mixture is then compressed.

Therefore the matrix structure of the tablet according to the invention is extremely simple, providing for easy industrial manufacture, since a single compression step of the mixture allows the production thereof without it being necessary to heat the compression tooling and/or the mixture before or during the actual compression step.

The matrix, in addition to the excipients of the matrix, may contain one or more excipients intended to promote the conducting of the compression process such as non-stick agents e.g. colloidal silica, talc, magnesium stearate, Polyethylene Glycol (PEG) or calcium stearate, or to improve the cohesion of the tablets during compression such as the binding agents conventionally used for this function, in particular starches, cellulose derivatives, or fillers, or lubricants, or plasticizers, or bulking agents or sweeteners or colouring agents.

The exceptional hardness of the tablets of the invention can be obtained without it being necessary to subject the mixture to be compressed (compression matrix and active ingredient) and/or the compression tooling (press) to a heating step prior to or during compression.

According to another embodiment of the invention, and when its particle size so permits, the active ingredient is mixed directly with the excipients forming the compression matrix, and the mixture is subsequently directly compressed.

Finally another possible embodiment of the invention is to mix the active ingredient with the excipient(s) of the compression matrix, then to granulate this mixture via wet or dry process to obtain directly compressible granules.

The tablets according to the invention may be in any shape or size allowing tablets at high hardness to be obtained.

The present invention is therefore adapted to the manufacture both of tablets containing a low dose of active ingredient and tablets containing a high dose of active ingredient.

The present invention further concerns the method for manufacturing the matrix tablets of the invention. This method comprises the following steps:
- mixing the active ingredient(s) with the excipient(s) of the matrix;
- optional granulation; and
- compressing the said mixture under conditions chosen so that the said tablet has a crush resistance of at least 4 MPa, advantageously at least 6 MPa,
- optional coating of the tablet.

Compression is performed on a rotary press. The compressing parameters must be chosen to allow tablets to be produced having hardness adapted to the present invention. However, it is not necessary to subject the mixture to be compressed or the compression tooling to any heating step before and/or during compression for the purpose of reaching the exceptional hardness observed in tablets according to the invention. The compression forces applied are between 5 kN and 60 kN, advantageously between 10 kN and 30 kN. They are chosen so that they are compatible with the material of the dies and can be used at industrial production rates, whilst allowing tablets to be obtained whose yield strength is higher than 4 MPa, and preferably higher than 6 MPa.

If the coating polymer of the tablet is a sustained-release polymer, the coated tablets according to the invention can advantageously undergo a curing phase of said coating polymer to guarantee its physical and chemical stability. This step is performed under controlled temperature conditions, lower than the melting point of the active ingredient for a controlled period of time which is dependent on the coating polymer and may be between 1 minute and several months, at a relative humidity of 50 to 99%. This step can be performed in an oven or perforated drum.

Multi-Layer Tablets

To overcome any problems of chemical compatibility between the active ingredient contained in the pharmaceutical form and some excipients of the formula, or between two active ingredients of the formula, the pharmaceutical form can advantageously be a multilayer form. Therefore the components which are not chemically compatible can be separated, for example xanthan gum can be contained in a layer with the active ingredient, and carbomer in another layer.

The crush resistance properties are maintained and the pharmaceutical form if it is reduced to powder allows extraction to be limited in aqueous/or hydro-alcoholic media in the same manner as the matrix form.

Micro-Tablets

By «micro-tablets» is meant tablets less than 4 mm in diameter.

A further subject of the invention is an oral pharmaceutical form comprising micro-tablets containing two populations of micro-tablets of identical outer appearance. The first population (1) comprises at least one gelling agent and at least one active ingredient possibly lending itself to addiction and the second population (2) comprises at least one gelling agent of carbomer type. This oral pharmaceutical form comprises micro-tablets whose misuse by crushing followed by injection or inhalation is impossible. These micro-tablets can be placed inside a capsule.

Another variant of the micro-tablets is to associate two populations formed of identical components but to vary the quantities of active ingredient and the excipients, and to mix these two populations of micro-tablets.

The method of manufacture of the micro-tablets is identical to the method described in the paragraph on matrix tablets.

EXAMPLES

Example 1

Comparative Example Lacking the Essential Elements of the Invention for Preparing a Matrix Tablet of 40 mg Oxycodone HCl Containing Xanthan Gum as Sole Gelling Agent Without any Carbomer or Gum Arabic

| Components | mg/tablet | Percentage |
|---|---|---|
| 1. Oxycodone, granulated | 43.68 | 29.12 |
| 2. Kollidon SR ® (PVA/PVP 80:20) | 75.27 | 50.18 |
| 3. Xanthan gum | 30.00 | 20.00 |
| 4. Syloid | 0.30 | 0.20 |
| 5. Magnesium stearate | 0.75 | 0.50 |
| Total | 150.00 | 100.00 |
| Hardness | 322 N | |
| Yeild strength | 7.7 MPa | |

In Example 1, components 1 to 4 were passed through a 500 μm sieve then mixed in a Turbula mixer for 10 min. Magnesium stearate was added and mixing was continued a further 1 min for lubrication. The mixture was then compressed directly on a Sviac rotary press equipped with round dies 7 mm in diameter, applying a force of 16 kN. The resulting hardness corresponds to yield strength higher than 7 MPa.

Percentages extracted in different media from the tablets obtained according to Example 1:

| Purified water | 0.1N HCl | 96% Ethanol |
|---|---|---|
| 0% | 0% | 58% |

When the tablet is crushed and dissolved in 10 mL volume of 96% ethanol, the amount of oxycodone HCl collected after filtration is 58% of the initial dose. Therefore the matrix tablet of 40 mg oxycodone HCl containing xanthan gum as sole gelling agent does not prevent extraction of the active ingredient in 96% ethanol.

Example 2

Comparative Example Lacking the Essential Elements of the Invention for Preparing a Matrix Tablet of 40 mg Oxycodone HCl Containing a Carbomer as Sole Gelling Agent Without Xanthan Gum

| Components | mg/tablet | Percentage |
|---|---|---|
| 1. Oxycodone, granulated | 43.55 | 28.46 |
| 2. Kollidon SR ® (PVA/PVP 80:20) | 81.19 | 53.07 |
| 3. Carbomer (Carbopol ®) | 27.00 | 17.65 |
| 4. Syloid | 0.36 | 0.24 |
| 5. Magnesium stearate | 0.90 | 0.59 |
| Total | 153.00 | 100.00 |
| Hardness | 417 N | |
| Yeild strength | 9.7 MPa | |

In Example 2, the mixture was prepared in identical manner to Example 1. The hardness of the tablets obtained under a force of 14 kN was higher than 400 N, the corresponding yield strength being more than 9 MPa.

Percentages extracted in different media from the tablets obtained according to Example 2:

| Purified water | 0.1N HCl | 96% Ethanol |
|---|---|---|
| 53% | 62% | 21% |

When the tablet prepared according to Example 2 is crushed and dissolved in 10 mL volume of 96% Ethanol, the amount of oxycodone HCl collected after filtration is 21% of the initial dose. On the other hand, the percentage in the aqueous media is greater than 50% of the dose.

Therefore the matrix tablet of 40 mg oxycodone HCl containing a carbomer as sole gelling agent does not prevent extraction of the active ingredient in 0.1 N HCl.

Example 3

Comparative Example Lacking the Essential Elements of the Invention, Based on Oxycontin®, Tablets Containing 40 mg Oxycodone HCl Percentages extracted in different media from Oxycontin® tablets

| Purified water | 96% Ethanol |
|---|---|
| 25% | 39% |

When the tablet is cut, crushed and dissolved in a 10 mL volume of 96% ethanol, the amount of oxycodone HCl collected after filtration is 39% of the initial dose. The amount collected after filtration in purified water is 25% of the initial dose.

These results therefore show that extraction of the active ingredient is possible. These results are improved by the invention.

Example 4

Matrix Tablet of 40 mg Oxycodone HCl According to the Invention Containing Xanthan Gum and a Carbomer as Gelling Agents

| Components | mg/tablet | Percentage |
|---|---|---|
| 1. Oxycodone, granulated | 43.68 | 25.69 |
| 2. Kollidon SR ® (PVA/PVP 80:20) | 74.13 | 43.61 |
| 3. Xanthan gum | 25.50 | 15.00 |
| 4. Carbomer (Carbopol ®) | 25.50 | 15.00 |
| 5. Syloid | 0.34 | 0.20 |
| 6. Magnesium stearate | 0.85 | 0.50 |
| Total | 170.00 | 100.00 |
| Hardness | 483 N | |
| Yeild strength | 10.5 N | |

In Example 4, components 1 to 5 were passed through a 500 μm sieve and mixed in a Turbula for 10 min. Magnesium stearate was added for a lubrication time of 1 min. The mixture was then compressed directly on a Sviac rotary press equipped with round dies 7 mm in diameter, applying a force of 16 kN. The resulting hardness was greater than 400 N, the corresponding yield strength being higher than 10 MPa.

Percentages extracted in different media from the tablets obtained in Example 3:

| Purified water | 0.1N HCl | 96% Ethanol |
|---|---|---|
| 0% | 8% | 23% |

When the tablet prepared according to Example 4 is crushed, dissolved in 10 mL volume of 96% ethanol, the amount of oxycodone HCl collected after filtration is 23% or the initial dose. The amount collected in the aqueous media is less than 10%.

Example 5

Matrix Tablet of 40 mg Oxycodone HCl According to the Invention Containing Xanthan Gum, a Carbomer and Sodium Bicarbonate

| Components | mg/tablet | Percentage |
|---|---|---|
| 1. Oxycodone, granulated | 43.55 | 22.92 |
| 2. Kollidon SR ® (PVA/PVP 80:20) | 88.12 | 46.38 |
| 3. Xanthan gum | 30.00 | 15.79 |
| 4. Carbomer (Carbopol ®) | 22.50 | 11.84 |
| 5. NaHCO3 | 4.50 | 2.37 |
| 6. Syloid | 0.38 | 0.20 |
| 7. Magnesium stearate | 0.95 | 0.50 |
| Total | 190.00 | 100.00 |
| Hardness | 474 N | |
| Yeild strength | 9.3 MPa | |

In Example 5, components 1 to 6 were passed through a 500 μm sieve and mixed in a Turbula mixer for 10 min. Magnesium stearate was added and mixing continued an additional 1 min for lubrication. The mixture was then directly compressed on a Sviac rotary press equipped with round dies 7 mm in diameter, applying a force of 13 kN. The resulting hardness was greater than 400 N, the corresponding yield strength being higher than 9 MPa.

Percentages extracted in different media from the tablets obtained according to Example 4:

| Purified water | 0.1N HCl | 96% Ethanol |
|---|---|---|
| 0% | 0% | 30% |

When the tablet is crushed, dissolved in 10 mL volume of 96% ethanol, the amount of oxycodone collected after filtration is 30% of the initial dose. The amount collected after filtration in the tested aqueous media is 0%.

Also, when the solution is not filtered and placed directly in a syringe having a 20 gauge needle, the viscosity of this solution is such that it does not pass through the needle.

In addition, the dissolution profiles generated in buffer media of pH 1.2 and pH 6.8 do not show any pH-dependence of the composition.

Example 6

Matrix Tablet of 40 mg Oxycodone HCl According to the Invention Containing Xanthan Gum, a Carbomer and Citric Acid

| Components | mg/tablet | Percentage |
|---|---|---|
| 1. Oxycodone, granulated | 43.55 | 22.92 |
| 2. Kollidon SR ® (PVA/PVP 80:20) | 88.12 | 46.38 |
| 3. Xanthan gum | 30.00 | 15.79 |
| 4. Carbomer (Carbopol ®) | 22.50 | 11.84 |
| 5. Citric acid | 4.50 | 2.37 |
| 6. Syloid | 0.38 | 0.20 |
| 7. Magnesium stearate | 0.95 | 0.50 |
| Total | 190.00 | 100.00 |
| Hardness | 440N | |
| Yield strength | 8.7 MPa | |

Example 6 was prepared in identical manner to Example 5. The resulting hardness was greater than 400 N, the corresponding yield strength being higher than 8 MPa.

Percentages extracted in different media from the tablets obtained according to Example 5:

| Purified water | 0.1N HCl | 96% Ethanol |
|---|---|---|
| 0% | 0% | 20% |

When the tablet is crushed, dissolving in 10 mL volume of 96% ethanol, the amount of oxycodone collected after filtration is 20% of the initial dose. The amount collected after filtration in the tested aqueous media is 0%.

In addition, when the solution is not filtered and placed directly in a syringe having a 20 gauge needle, the viscosity of this solution is such that it does not pass through the needle.

Also, the dissolution profiles generated in buffer media of pH 1.2 and pH 6.8 do not show any pH-dependence of the composition.

Example 7

Matrix Tablet of 32 mg Hydromorphone According to the Invention Containing Xanthan Gum, a Carbomer and Citric Acid

| Components | mg/tablet | Percentage |
|---|---|---|
| 1. Hydromorphone | 32.00 | 25.60 |
| 2. Kollidon SR ® (PVA/PVP 80:20) | 35.12 | 28.10 |
| 3. Xanthan gum | 30.00 | 24.00 |
| 4. Carbomer (Carbopol ®) | 22.50 | 18.00 |
| 5. Citric acid | 4.50 | 3.60 |
| 6. Syloid | 0.25 | 0.20 |
| 7. Magnesium stearate | 0.63 | 0.50 |
| Total | 125.00 | 100.00 |
| Hardness | 268N | |
| Yield strength | 7.7 MPa | |

Example 7 was prepared in identical manner to Example 6. The resulting hardness corresponded to yield strength of more than 7 MPa.

Percentages extracted in different media from the tablets obtained according to Example 6:

| Purified water | 0.1N HCl | 96% Ethanol |
|---|---|---|
| 0% | 6% | 20% |

When the tablet is crushed, dissolved in 10 mL volume of 96% ethanol, the amount of hydromorphone collected after filtration is 20% of the initial dose. The amount collected after filtration in the tested aqueous media is less than 10%.

Example 8

Multilayer Tablet of 40 mg Oxycodone HCl According to the Invention Containing Xanthan Gum, a Carbomer and Citric Acid

| Components | mg/tablet | % |
|---|---|---|
| Oxycodone HCl, granulated | 43.55 | 16.40 |
| Kollidon SR ® (PVA/PVP 80:20) | 88.12 | 33.19 |
| Xanthan gum | 30.00 | 11.30 |
| Syloid | 0.32 | 0.12 |
| Magnesium stearate | 0.80 | 0.30 |
| TOTAL layer 1 | 162.79 | 61.32 |
| Kollidon SR ® (PVA/PVP 80:20) | 30.00 | 11.30 |
| Xanthan gum | 15.00 | 5.65 |
| Syloid | 0.10 | 0.04 |
| Magnesium stearate | 0.22 | 0.08 |
| TOTAL layer 2 | 45.32 | 17.07 |
| Carbomer (Carbopol ®) | 22.50 | 8.47 |
| Citric acid | 4.50 | 1.69 |
| Kollidon SR ® (PVA/PVP 80:20) | 30.00 | 11.30 |
| Syloid | 0.11 | 0.04 |
| Magnesium stearate | 0.28 | 0.11 |
| TOTAL layer 3 | 57.39 | 21.62 |
| TOTAL | 265.50 | 100.00 |
| Hardness | 430N | |
| Yield strength | 6.7 MPa | |

In Example 8, each layer was mixed separately in the same manner as for the mixtures in the preceding examples.

The tablets obtained on a rotary press equipped with dies of diameter 8.5 mm had a final hardness greater than 400 N, the corresponding yield strength being higher than 6 MPa.

Percentages extracted in different media from the tablets obtained according to Example 7:

| Purified water | 0.1N HCl | 96% Ethanol |
|---|---|---|
| 0% | 0% | 26% |

When the multilayer tablet is crushed, dissolved in 10 mL volume of 96% ethanol, the amount of oxycodone HCl collected after filtration is 26% of the initial dose. The amount collected after filtration in the tested aqueous media is 0%.

The conclude, the presence of xanthan gum and of Carbopol or gum arabic is essential to limit the release of active ingredient into an aqueous or hydro-alcoholic medium.

Example 9

Micro-Tablets of Morphine Sulfate: Association of 2 Different Populations of Micro-Tablets Containing a Unit Dose of 10 mg Morphine Sulfate and Comprising Xanthan Gum, a Carbomer and pH Stabilizer Population 1

| Composition | mg/tablet | % |
|---|---|---|
| 1. Morphine Sulfate | 10.00 | 40.00 |
| 2. Kollidon SR ® (PVA/PVP 80:20) | 10.50 | 42.00 |
| 3. Xanthan Gum | 4.00 | 16.00 |
| 4. Microcrystalline Cellulose (Avicel PH102) | 0.13 | 0.52 |
| 5. Syloid 244 FP | 0.12 | 0.48 |
| 6. Magnesium stearate | 0.25 | 1.00 |
| Total | 25.00 | 100.00 |
| Hardness | 111N | |
| Yield strength | 7.3 MPa | |

Population 2

| Composition | mg/tablet | % |
|---|---|---|
| 1. Carbopol ® 71G | 18.500 | 74.0 |
| 2. Citric acid or Sodium Bicarbonate | 3.700 | 14.8 |
| 3. Microcrystalline cellulose | 2.550 | 10.2 |
| 4. Syloid 244 FP | 0.125 | 0.5 |
| 5. Magnesium stearate | 0.125 | 0.5 |
| Total | 25.000 | 100.0 |

In Example 9, population 1 of micro-tablets was prepared in the following manner: components 1 and 4 were passed through a 500 μm sieve and mixed in a Turbula mixer for 10 min. Magnesium stearate was added and mixing continued a further 1 min for lubrication. The mixture was then directly compressed on a Sviac rotary press equipped with round dies 3 mm in diameter, applying a force of 2 kN. The resulting hardness was greater than 100 N, the corresponding yield strength being higher than 7 MPa.

Population 2 was prepared in similar manner: components 1 to 4 were sieved before being mixed in a Turbula mixer for 5 min. Magnesium stearate was added and mixing continued a further 1 min for lubrication.

The two populations were associated in the following manner: 6 micro-tablets of population 1 and 2 micro-tablets of population 2, giving the following unit composition (content of one capsule):

| | 6 micro-tablets of population 1 + 2 micro-tablets of population 2 | |
|---|---|---|
| Composition | mg | % |
| Morphine sulfate | 60.0 | 30.0 |
| Kollidon SR ® (PVA/PVP 80:20) | 63.0 | 31.5 |
| Xanthan gum | 24.0 | 12.0 |
| Carbopol 71G | 37.0 | 18.5 |
| pH stabilizer | 7.4 | 3.7 |
| Avicel PH102 | 5.8 | 2.9 |
| Syloid 244 FP | 1.0 | 0.5 |
| Magnesium stearate | 1.8 | 0.9 |
| Total | 200.0 | 100.0 |

Percentages extracted in different media from the micro-tablets obtained according to Example 9 when the pH stabilizer is citric acid:

| Purified water | 0.1N HCl | 96% Ethanol |
|---|---|---|
| 2% | 11% | 6% |

Percentages extracted in different media from the micro-tablets obtained according to Example 9 when the pH stabilizer is sodium bicarbonate:

| Purified water | 0.1N HCl | 96% Ethanol |
|---|---|---|
| 0% | 10% | 6% |

When the micro-tablets in Example 9 are crushed, dissolved in 10 mL volume of 96% ethanol, the amount of morphine sulfate collected after filtration is less than 10% of the initial dose, whether in water or in 96% ethanol, with both of these pH stabilizers. The amount collected after filtration in 0.1 N HCl is in the order of 10% for both pH stabilizers.

Example 10

Micro-Tablets of Morphine Sulfate: Association of 2 Populations Differing in the Ratio of the Components In Example 10, two populations of identical composition to populations 1 and 2 in Example 9 were associated as follows: 10 micro-tablets of population 1 and 1 micro-tablet of population 2, which led to the following unit composition (content of one capsule):

| Composition | 10 micro-tablets of population 1 + 1 micro-tablet of population 2 | |
| --- | --- | --- |
| | mg | % |
| Morphine sulfate | 100.0 | 36.4 |
| Kollidon SR ® (PVA/PVP 80:20) | 105.0 | 38.2 |
| Xanthan gum | 40.0 | 14.5 |
| Carbopol 71G | 18.5 | 6.7 |
| pH stabilizer | 3.7 | 1.3 |
| Avicel PH102 | 3.9 | 1.4 |
| Syloid 244 FP | 1.3 | 0.5 |
| Magnesium stearate | 2.6 | 1.0 |
| Total | 275.0 | 100.0 |

Percentages extracted in different media from the association of micro-tablets obtained according to Example 10 when the pH stabilizer is citric acid:

| Purified water | 0.1N HCl | 96% Ethanol |
| --- | --- | --- |
| 0% | 3% | 7% |

Percentages extracted in different media from the association of micro-tablets obtained according to Example 10 when the pH stabilizer is sodium bicarbonate:

| Purified water | 0.1N HCl | 96% Ethanol |
| --- | --- | --- |
| 0% | 2% | 6% |

When the micro-tablets of Example 9 are crushed, dissolved in 10 mL volume of 96% ethanol, the amount of morphine sulfate collected after filtration is 10% or lower of the initial dose, in the three media.

What is claimed is:

1. An oral pharmaceutical composition in the form of a sustained-release matrix tablet, the matrix consisting of:
   from 10% to 40% by weight relative to the total weight of the composition of at least one active ingredient likely to be misused for drug addiction purposes; and
   a combination of:
      from 20% to 60% by weight relative to the total weight of the composition of a mixture of polyvinyl acetate and polyvinylpyrrolidone,
      from 15% to 25% by weight relative to the total weight of the composition of xanthan gum,
      from 10% to 30% by weight relative to the total weight of the composition of a carbomer,
      from 1% to 20% by weight relative to the total weight of the composition of a pH stabilizing agent, and
      at least one anti-adherent agent,
   wherein the carbomer is a polymer of acrylic acid of high molecular weight cross-linked with allyl sucrose or allyl ethers of pentaerythritol;
   wherein the pH stabilizing agent comprises at least one compound chosen from: citric acid and sodium bicarbonate;
   wherein said combination prevents misuse by injection by forming a gel trapping the active ingredient and having a viscosity such that the gel cannot pass through a needle when the composition is reduced to powder and dissolved in an injectable volume of an aqueous or hydro-alcoholic solution, and such that the amount of active ingredient extracted in an aqueous medium is lower than 25%; and
   wherein the active principle is released over a period of more than 20 hours, and wherein said tablet has a yield strength higher than 6 MPa.

2. The pharmaceutical composition according to claim 1, wherein the said active ingredient(s) are selected from the group consisting of psychotropics, antipsychotics, tranquillizers, hypnotics, analgesics and anxiolytics.

3. The pharmaceutical composition according to claim 1, wherein the said active ingredient(s) selected from the group consisting of morphine, oxycodone, hydrocodone, hydromorphone, oxymorphone, tramadol, methadone, codeine, fentanyl and buprenorphine, cannabinoids, cocaine, amphetamines their pharmaceutically acceptable salts and derivatives.

4. The pharmaceutical composition according to claim 1, wherein the ratio of polyvinyl acetate and polyvinylpyrrolidone is from (95:5) to (70:30).

5. The pharmaceutical composition according to claim 1, wherein the viscosity of the gel trapping the active ingredient is such that the gel cannot pass through a 20-gauge needle.

6. A method for combatting misuse by injection for drug addiction purposes comprising administering a pharmaceutical composition according to claim 1 to a patient in need thereof.

7. A method for combatting misuse via nasal route for drug addiction purposes comprising administering a pharmaceutical composition according to claim 1 to a patient in need thereof.

8. A method for combatting misuse via oral route for drug addiction purposes comprising administering a pharmaceutical composition according to claim 1 to a patient in need thereof.

9. A method for combatting accidental misuse for drug addiction purposes comprising administering a pharmaceutical composition according to claim 1 to a patient in need thereof.

10. A method of treatment comprising administering once daily of a pharmaceutical composition according to claim 1 to a patient in need thereof.

11. A method of treatment comprising administering twice daily of a pharmaceutical composition according to claim 1 to a patient in need thereof.

12. A method for manufacturing the sustained-release matrix tablet according to claim 1, the method comprising:
   mixing the at least one active ingredient with the combination to provide a mixture;
   optionally granulating the mixture; and
   compressing the mixture under conditions chosen so that the tablet has a crush resistance of at least 6 MPa.

13. The method according to claim 12, wherein compressing the mixture is performed without heating the mixture and without heating a tool for compressing before or during compression.

14. The method according to claim 12, further comprising coating the matrix tablet.

15. The method according to claim 14, further comprising curing the outer coating.

* * * * *